United States Patent [19]

Lontz

[11] Patent Number: 5,420,250

[45] Date of Patent: May 30, 1995

[54] PHASE TRANSFER PROCESS FOR PRODUCING NATIVE PLASMA PROTEIN CONCENTRATES

[75] Inventor: John F. Lontz, Wilmington, Del.

[73] Assignee: Fibrin Corporation, Wilmington, Del.

[21] Appl. No.: 44,585

[22] Filed: Apr. 8, 1993

Related U.S. Application Data

[63] Continuation-in-part of Ser. No. 855,752, Mar. 23, 1992, abandoned, which is a continuation-in-part of Ser. No. 759,698, Sep. 9, 1991, abandoned, which is a continuation-in-part of Ser. No. 562,839, Aug. 6, 1990, abandoned.

[51] Int. Cl.⁶ .................. A61K 38/36; C07K 1/30; C07K 14/745; C07K 14/75
[52] U.S. Cl. .................. 530/381; 530/380; 530/382; 530/427; 530/830
[58] Field of Search .................. 128/DIG. 27; 106/124, 106/125; 514/2, 8, 12, 21, 802; 530/363, 364, 381, 382, 383, 384, 412, 414, 427, 830, 380

[56] References Cited

U.S. PATENT DOCUMENTS

| | | | |
|---|---|---|---|
| 2,492,458 | 12/1944 | Bering et al. | 530/382 |
| 3,297,532 | 1/1967 | Jones | 530/830 |
| 3,523,870 | 8/1970 | Gerendas et al. | 106/124 |
| 4,216,205 | 8/1980 | Radowitz | 530/380 |
| 4,278,592 | 7/1981 | Seufert et al. | 530/382 |
| 4,289,691 | 9/1981 | Rock et al. | 530/383 |
| 4,298,598 | 11/1981 | Schwarz | 514/2 |
| 4,359,049 | 11/1982 | Redl et al. | 604/82 |
| 4,362,567 | 12/1982 | Schwarz et al. | 106/157 |
| 4,377,572 | 3/1983 | Linnau | 514/2 |
| 4,414,976 | 11/1983 | Linnau | 530/362 |
| 4,427,650 | 1/1984 | Stroetmann | 530/382 |
| 4,600,574 | 7/1986 | Lindner | 424/448 |
| 4,608,254 | 8/1986 | Philapitsch | 424/530 |
| 4,627,879 | 12/1986 | Dresdale et al. | 106/124 |
| 4,631,055 | 12/1986 | Habison | 604/82 |
| 4,638,048 | 1/1987 | Foster | 530/830 |
| 4,650,678 | 3/1987 | Fuhge et al. | 514/2 |
| 4,735,616 | 4/1988 | Eible | 604/191 |
| 4,909,251 | 3/1990 | Seelich | 606/213 |
| 4,928,603 | 5/1990 | Dresdale et al. | 106/124 |
| 4,960,757 | 10/1990 | Kumpe et al. | 514/21 |
| 5,321,126 | 6/1994 | van Dommelen et al. | 530/382 |

FOREIGN PATENT DOCUMENTS

WO8601814 3/1986 WIPO.

OTHER PUBLICATIONS

Anonymous, Freezing and Thawing Serum Cells, Technical Bulletin, *Art to Science*, vol. 5, No. 2, HyClone Laboratories, Logan, Utah. 1986.

ASTM Designation D-413—82 Standard Test Methods for Rubber Property—to Flexible Substrate, pp. 70, 71, 73 and 74, 1990.

ASTM Designation F-639-79:85 Standard Specification for Polyethylene Plastics for Medical Applications, p. 164. 1990.

ASTM Designation D-638—68 Standard Method of Test for Tensile Properties of Plastics, p. 189, 195-197, 1990.

Brands et al., Preservation of the Ruptured Spleen by Gluing with Concentrated Fibrinogen. Experimental and Clinical Results. *World J. Surg.*, vol. 6, pp. 366-368, 1982.

Brodniewicz-Proba et al., Modified Glycine Precipitation Technique for the Preparation of Factor VIII Concentrate of High Purity and High Stability Vox-Sang 52:10-14 (1987).

(List continued on next page.)

*Primary Examiner*—Jeffrey E. Russel
*Attorney, Agent, or Firm*—Fish & Richardson

[57] ABSTRACT

Cryoprecipitated mammalian plasma proteins with associated glycoproteins, polysaccharides, and numerous other macromolecular entities are transferred directly in the course of controlled thawing and centrifuging from native plasma phase across the boundary layer into a pre-prepared substrate transfer medium at sustained solidus—liquidus equilibrium regulated to residual icing from about 5 weight percent to about 95 weight percent to produce cryoprecipitates with enhanced productivity and enhanced qualifications for in vivo tissue bonding applications.

12 Claims, No Drawings

OTHER PUBLICATIONS

Castillo et al. Prothrombin Times and Clottable Fibrinogen Determination on An Automated Coagulation Laboratrory. *Thrombosis Res.*, pp. 213, 215, 217, 219, 1989.

Cohn et al., *J. Am. Chem. Soc.*, vol. 68, pp. 459–475, 1946.

Conte et al., Infection–Control Guidelines For Patients with the Acquired Immunodeficiency Syndrome (AIDS), *The New Eng. Jour. of Med*, Sep. 1983, 740–744.

Dresdale et al., Hemostatic Effectiveness of Fibrin Glue Derived from Single–Donor Fresh Frozen Plasma. *Ann. Thor. Surg.*, vol. 40, p. 385–387, 1985.

Dresdale et al., Preparation of Fibrin Glue from Single–Donor Fresh–frozen Plasma, *Surgery*, vol. 97, pp. 750–754, 1985.

Edsall et al., *J. Biol. Chem.*, vol. 191, pp. 735–756, 1951.

Epstein, et al., Current Safety of Clotting Factor Concentrates *Arch. Pathol. Lab. Med.* vol. 114; 335–340 1990.

Epstein, G. H. et al., A New Autologous Fibrinogen–Based Adhesive for Otologic Surgery. *Ann. Otol. Rhinol Laryngol*, vol. 95, pp. 40–45, 1986.

Farrugia et al., "Studies on the procurement of blood coagulation factor VIII . . . ", *J. Clin. Pathol.* vol. 38, pp. 433–437, 1985.

*FDA Drug Bulletin* vol. 8, No. 2, pp. 15–16, Mar. Apr. 1978.

Gestring, Gidon F., Autologous Fibrinogen for Tissue–Adhesion, *Hemostasis and Embolization* pp. 294–296, and 303, 1982.

Grey, R. G. Fibrin as a Hemostatic in Cerebral Surgery. *Surg. Gynecol. Obstr.* vol. 21, 452–454, 1915.

Hammerstein, O. Arch. Gesamte Physiol, *Menschen Tier*, vol. 19, pp. 563–622, 1879.

Holmes et al., a–Proteins in Human Cell Cult., *In Vitro*, vol. 15, pp. 522–530, 1979.

Klein, J., The Interdiffusion of Polymers, *Science*, vol. 250, pp. 640–641, 1990.

Kram, H. B., et al., "Fibrin Glue Sealing of Polyetetrafluoroethylene Vascular Graft Anastomoses. Comparison with oxidized Cellulose", *J. Vascular Surgery*, 1988, 8:563–568.

Matras et al., Zur Nachlosen Interfaszikularen Nerventransplantation in Tierexperiment. *Wien. Med/Wochenschr.* vol. 122, pp. 517–521, 1972.

Putnam, Frank W., Ed. *The Plasma Proteins*, Ch 2. vol 1, Pennell, Robert B. Fractionation and Isolation and Purified Components by Precipitation Methods, p. 9–50 1960.

Putnam, F. W., Ed. *The Plasma Proteins*, 2nd Ed., Section 3. Doolittle, R. F., Fibrinogen and Fibrin pp. 110–111, 116–161.

Putnam, F. W., Ed. *The Plasma Proteins*, 2nd Ed., Section 4. Clamp, J. R. Structure and Functions, pp. 163–211, esp. 164, 173 and 174, 1975.

Siedentop et al., Autologous Fibrin Tissue Adhesive, *Laryngoscopy*, vol. 95, pp. 1074–1076, 1985.

Spotnitz et al., Fibrin Glue from Stored Human Plasma, *The American Surgeon*, Aug. 1987, No. 8; 460–462.

Lozina–Lozinskii, Studies In Cryobiology, pp. 195–203.

Gestring et al, Autologous Fibrinogen for Tissue–Adhesion, etc. Vas. Surg., vol. 17 (1982), pp. 294–295.

Dresdale et al, Preparation of Fibrin Glue, Etc. Surgery, vol. 96 (1985), pp. 750–751.

Siedentrop et al, Autologous Fibrin Tissue Adhesive, Laryngoscopy, vol. 95 (1985), pp. 1074–1075.

PHASE TRANSFER PROCESS FOR PRODUCING NATIVE PLASMA PROTEIN CONCENTRATES

RELATED APPLICATIONS

This application is a continuation-in-part of application Ser. No. 07/855,752, filed Mar. 23, 1992, now abandoned, which is a continuation-in-part of application Ser. No. 07/759,698, filed Sep. 9, 1991, now abandoned, which is a continuation-in-part of application Ser. No. 07/562,839, filed Aug. 6, 1990, now abandoned.

FIELD OF INVENTION

This invention is in the field of processes for producing native cryoprecipitated plasma protein concentrates applying a controlled thermal drift from cryofreezing through thawing to ultimate centrifugation wherein the cryoprecipitate is transferred from the plasma or serum phase into a preprepared transfer phase of a viscous substrate formulated with natural biological and synthetic macromolecular modifiers and stabilizers as novel products of enhanced viscosity and tissue adhesion bonding properties for use in replacing or supplementing surgical suturing.

BACKGROUND ART

Cryoprecipitation is a long established means for preparing fibrinogen concentrates from human and other mammalian plasma as fibrin sealants in surgical repair. The ubiquitous physiological role of fibrinogen and fibrin in the phenomena and mechanism of coagulation, internal restructuring, wound healing, and tissue repair has been extended over the past scores of years to a concentrate, processed variously from plasma for applied tissue bonding under such descriptive terms as fibrin glue, fibrin adhesive, fibrin weld, fibrin sealant, and so on.

The clinical use of fibrinogen prepared from plasma by various methods of cryoprecipitation and by chemical insolubilization has gradually emerged for such early uses as hemostyptic adhesive powder with small open vessels (Bergel, S., Deutsch Med. Wochenschr. pp. 633–665, 1909), as a hemostatic agent in cerebral surgery (Grey, E. G., Surg. Gyn. Obst., Vol. 21, pp. 425–454, 1915), in suturing peripheral nerves (Matras, H. et al., Wien. Med. Wochenschr., 1972), and gradually expanded to the repair of traumatized tissues (Brands, W. et al., World J. Surg., Vol. 6, pp. 366–368, 1982), and anastomoses or restructuring of cardiovascular, colon, bronchial sections, severed nerve endings, and other anatomical discontinuities currently in widespread practice often replacing or augmenting conventional suturing. In such clinical applications, the native fibrinogen content in plasma averages 513 milligrams per decaliter (mg/dcl) according to standard clinical assays, ranging from as low 229 mg/dcl to as high as 742 mg/dcl, based on photometric measurements of turbidity from clotting (Castillo, J. B., et al. Thrombosis Res., Vol. 55, pp. 213–219, 1989). In a typical reference (Dresdale, A. et al., Surgery, Vol. 97, p. 751, (1985); also published PCT patent application WO 86/01814), the stated sequence of cryofreezing, thawing, and centrifuging produces a fibrinogen concentrate of extremely low productivity of only 2.16 percent (2160 mgm/dcl). The resulting fibrinogen concentrates of the prior art are too low in solids content, are further diluted with added thrombin for conversion to fibrin state, and therefore lacking viscous contact tenacity of low viscosity, very much like that of water and appreciably lower than of the initial plasma from which it derived.

In order to correct and improve upon the needed productivity with defined and specified qualifications tests and performance standards, lacking in or unattainable from currently available methods, a novel and more efficient and accountable process was devised as described in the applications Ser. No. 07/562,839, now abandoned, hereinafter '839, and Ser. No. 07/855,752, now abandoned, hereinafter '752. In the '839 application, the principal objective was to attain a higher level Of solids content in fibrinogen concentrates by applying controlled thermal drift throughout the integrated cryoprecipitation, thawing, and centrifuging steps. This process resulted in an unexpected increased productivity, and enhanced adhesion and bonding, as demonstrated by in vivo animal tissue adhesion bonding, wound healing, and restored biomechanical tissue integrity. None of the prior art provides such essential descriptive details on process productivity, process efficiency, and product qualifications with supporting tests for a broadened range of the cryoprecipitated native proteins supplemented with such macromolecular structures as polysaccharides, glycoproteins, and the like for biomedical applications in surgical tissue reconstruction.

In support of the inventions described in this and the '752 and '839 applications, cryoprecipitated plasma product qualification tests have been devised to serve as a basis for specifications and uniform performance standards for regulatory compliance in direct clinical applications, for large scale production from pooled plasma, and for autologous small scale single lot preparations of enhanced plasma protein concentrates. The process of the present invention, which prepares fibrinogen concentrates, is especially important in view of the prevalent risk of viral infections, notably numerous forms of hepatitis and human immune deficiency virus (HIV), from pooled or single donor non-autologous sources.

This application extends the thermal drift process further with a novel intervening step wherein the cryoprecipitate is added to a transfer phase containing naturally occurring or synthetic macromolecular and functional entities of relatively low molecular weight. The macromolecular entities are intended to enhance contact adhesion to tissues and to assure safe and effective in vivo tissue bonding, healing, and restored biomechanical integrity. The phase transfer media includes antibiotic, antifibrinolytic, anticoagulant supplements, and preservatives and stabilizers, for extended storage stability shelf life.

Apart from cryoprecipitation, alternate means for separating and concentrating fibrinogen or plasma protein in currently available methods involve chemical or solvent precipitating procedures by admixtures with concentrated salt solutions, such as semi-saturated sodium chloride and saturated ammonium sulfate, and by cold ethanol and other low molecular weight organic compounds, notably amino acids such glycine, and numerous combinations thereof.

However, these chemical precipitating methods impose varying degrees of denaturation (Putnam text, The Plasma Proteins, Academic Press, Section 3,1975) in contrast to non-chemical cryoprecipitation. Chemical precipitations with organic solvents or additives are used mostly for preparing high purity fibrinogen stripped of the natively associated symbiotic plasma proteins, notably the low molecular weight proteins, glycoproteins, and polysaccharides which remain dissolved by virtue of higher degree of solubility. Consequently, it is only possible slowly, at elevated temperatures and only in low concentration, to re-dissolve the chemically precipitated and thusly denatured fibrinogen and plasma proteins from lyophilized form; the solubility of the lyophilized denatured fibrinogen can be increased with specific chemical formulation with decrease in viscosity but still in denatured state. The cryoprecipitation process of the invention distinguishes clearly from chemical precipitation by preserving the solubility of the cryoprecipitates, without the need for any re-dissolution, to as high as 40 percent protein solids content with corresponding increase in viscosity.

In the course of chemical preparations of fibrinogen concentrates, the native, plasma proteins include valuable associated mucopolysaccharides and glycoproteins in their varied acetylated and aminic forms of mucopolysaccharides, discarded according to the practices of the prior art in the course of the chemical preparations of fibrinogen for fibrin sealants. Now with the present and preceding :inventions, it has been discovered that the discarded molecular entities cryoprecipitated from re-cycled supernatants continue to provide concentrates with significantly enhanced viscous adhesion in tissue bonding in actual in vivo tissue and in vivo animal tests as described in the previous application, Ser. No. 07/855,752, now abandoned, and as shown in ensuing examples of this application. The essential processing steps of this invention are discoursed as follows and detailed with a number of Examples typifying the preferred embodiment with different transfer media and different mammalian plasma types supplementations.

Cryoprecipitation

Cryoprecipitation heretofore has not been generally recognized as a preferred method for making enhanced high solids fibrinogen concentrationis with retained associated native mucoproteins and mucopolysaccharides for adhesive viscous quality in preference to chemical fractional precipitation that specifically strip off the solubilized associated mucoproteins and mucopolysaccharides. Such adventitious chemical stripping can be expected to impose major physical conformational changes in the molecular form and shape of native fibrinogen structure (see Putnam text, The Plasma Proteins, Section 3 and Section 4, Academic Press, 1975) commonly referred to as denaturing with marked changes in physical, chemical and biological characteristics.

In the prior art cryoprecipitation starts off with cryofreezing, that is, deep freezing down to about −80° Centigrade with a wide range of temperature-time variables but with no indication of the effect of the varied temperature-time kinetics on productivity or on measured, quantitized product properties or specifications as described and assessed in the preceding application Ser. No. 07/855,752, filed Mar. 23, 1992, now abandoned. Rather the prior art predisposes to infer that longer periods of cryofreezing and thawing are necessary for attaining some undefined merit and with no measures of productivity and product quality of the fibrinogen tissue sealant with or without the numerous and diverse associated native plasma proteins and polysaccharides. For instance, the clinical preparations in the prior art commence with cryofreezing at −80° C., specified for at least 6 hours (Gestring, G. F., et al., Vascular Surgery, p. 295, 1983); later this was increased to at least 18 hours (Dresdale, A., et al., Annals of Thoracic Surgery, Vol. 40, p. 885, 1985); and again later for at least 24 hours (Spotnitz, W. D., et al., American Surgeon, p. 461, 1937). Clearly this teaching to increase the cryofreezing time is misleading. Furthermore these prior art prolonged time schedules are prohibitive for needs in autologous emergency tissue sealing for it was discovered, as described in application Ser. No. 07/562,839, on Aug. 6, 1990, now abandoned, on process engineering for producing fibrinogen concentrates, that the cryofreezing time at −80° C. can be reduced down to 1 hour and less for expedient, emergency surgical needs with specified, substantially increased productivity hitherto unstated in the prior art with regard to yield and solids content of stained fibrinogen concentrate.

In the present invention, an innovative, intervening feature is provided with the direct transfer of the native cryoprecipitate from the plasma following the cryofreezing with continued solubilization into a pre-prepared transfer medium throughout the thawing and centrifugation of tile engineering process system. As described in the original application following cryofreezing during phase transfer, controlled thawing is the next essential and critical process step during which the solid heterogeneous crystalline-like frozen mush is transformed into the two phases. The upper supernatant phase comprises residual icing, also referred to herein as icing, in the form of a glacialized homogeneous solid plug of ice transformed from the cryofrozen mush. This residual icing has not been recognized in the known prior art as a controlling feature for process productivity within the range from about 5 weight percent to about 95 weight percent icing depending upon the applied temperature-time thermal drift schedule through the solidus—liquidus transition temperature.

With prolonged thawing, either as the usual separate process or simultaneously during centrifuging, the ice progressively melts during the thermal drift along with restricted re-dissolving of the low and intermediate molecular weight proteins, glycoproteins, and mucopolysaccharides depending upon the residual icing. The control of the thermal drift from cryofreezing is critical to the quality of the cryoprecipitate concentrate, the solids concentration assay and the distribution of the numerous associated plasma proteins and mucopolysaccharides through the solidus—liquidus equilibrium transition temperature depicted as follows:

| Process phases | | |
| --- | --- | --- |
| cryoprecipitation | thawing −0° C. → >0° C. | centrifugation |
| (solidus) | (de-icing) | (liquidus) | wherein the solid plasma releases the cryoprecipitated insoluble fibrinogen and its relatively soluble associated proteins and mucopolysaccharides, which are important for enhanced tissues bonding, retained with the cryoprecipitate concentrate by the control of the level of residual icing for attaining the desired solids contents in the concentrates. The ratio of the fibrinogen to the associated plasma components proteins and mucopolysaccharides is thus regulated by the time-controlled thermal drift of the solidus—liquidus transition as the more soluble plasma components re-dissolve with increasing time at the thawing equilibrium temperature. Each component has its own solidus—liquidus transition temperature. Thus, various components may be released and/or retained depending on the selected solidus—liquidus transition temperature.

The associated plasma macromolecular proteins serve as intrinsic bioadhesives, characterized as mucoproteins and chemically known as glycoproteins indigenous with fibrinogen and are intended to be retained as component portions of the various cryoprecipitated compositions of the concentrates. Included in the cryoprecipitated products are numerous hematological factors involved in the clotting mechanism and cell growth factors involved in the healing of the rejoined tissue incisions for which the macromolecular proteins contribute enhanced viscosity for the peremptory handling and dispensing qualifications. All of these ancillary indigenous plasma components, considered valuable and indispensable for firm tissue bonding, are returnable as part of the cryoprecipitate concentrates by restricting their dissolution with the temperature-time thermal drift control of the process through the thawing phase at the transition equilibrium temperature.

Thawing Control

The extent of thawing by this invention is controlled by the de-icing in the supernatant phase by the measure of residual glacialized ice retained in the form of a solid plug, hitherto not recognized in the prior art. The ice plug by reason of its slightly lower density than its ice water phase floats to the top of the supernatant fluid, is readily withdrawn, weighed or measured as thawed weight or volume, and rated in terms of percent residual icing from the initial weight or volume of plasma. The extent of thawing, based on the percent residual icing, is thus regulated by applying appropriate temperature-time schedule either as a separate thawing procedure or preferably simultaneously with the centrifuging time. The overall process time thus provides a measure of process time-efficiency while the productivity is determined as the product of (a) the cryoprecipitate yield in grams multiplied by (b) the percent solids assay converted to and expressed in milligrams; these two items of materials constitute the indispensable means for further assessments of materials balance and process improvements from the important basic solids assay of the initial plasma. These productivity items in turn affect the attained product qualifications of this invention measured principally in terms of measured viscosity and ultimate tissue bonding strengths.

Thus the extent of the retention of the fibrinogen associated plasma components is dependent upon the applied thermal drift time from the cryogenic state through the icing equilibrium with minimal prolongation of time in the liquidus watery phase in the developing supernatant phase during which the native associated mucopoly-saccharides, mucoproteins and hematological factors continue to redissolve from the cryoprecipitated state during prolonged thawing time. In this regard the redissolved associated plasma components can be recovered by recycling the separated, decanted supernatant plasma or serum by repeating the complete sequence of the thermal drift from cryofreezing to thawing, separately or preferably simultaneously with the centrifuging operation.

The thawing temperature-time schedule according to published prior art methods is not specific, ignores the critical temperature-time variables, and in no instances provide correlations to either the productivity in terms of an appropriate materials balance or to product qualifications of the attained plasma cryoprecipitate for effective tissue bonding or tissue sealant applications. For instance, the prior art varies from such indefinite temperature-time kinetics of thawing such as at +4° C. "when liquid" (Gestring, supra); at 4° C. "for several hours" (Dresdale, supra); and at 1° C. to 6° C. for 20 hours (Siedentop, K. H., et al., Laryngoscope, Vol. 95, p. 1075, 1985). In no instance of this typical prior art is there indication of the concentrate productivity in terms of gram yield, percent solids content, and corresponding dry solids content milligrams, as a matter of providing the customary engineering materials accounting or balance for assessing process efficiency with reference to the solids materials contents of the initial plasma from which the cryoprecipitate is derived in a single cycle fraction (such as Fraction I, II, III, etc.) by repeated recycling of the separated supernatants.

In the published cited references, prolonged thawing can only lead to continuing redissolving of the valuable and useful plasma proteins but in no instances is there any indication of residual icing during the temperature-time thermal drift. The references disclose the inordinate loss of valuable fibrinogen and its associated plasma entities notably the proteins and useful mucopolysaccharides with fibrinogen concentrates as low as 2.16 percent content (Dresdale, supra). The need for minimizing the temperature-time thermal drift is made evident by controlling the solidus—liquidus temperature-time to the retention of residual icing within a range from about 5 weight percent to about 95 weight percent. This is to allow maximum thawing at the equilibrium transition temperature on the one hand and for minimal redissolving of the cryoprecipitates on the other hand.

Centrifuging

Following and during thawing, the cryoprecipitate is sedimented further into the transfer phase medium from the thawing plasma by means of centrifugation into the lower pre-prepared viscous phase comprising a solution of natural and synthetic macromolecular polysaccharide of various chemical configurations in such media as sterile water, normal saline, Ringers lactate solution, spent supernatant fluids, and even fractional portions of the plasma. In addition to providing enhanced viscous adhesion and supplementation preservatives, stabilizing agents, antibiotics, and so on, these different phase transfer media, with or without physiological additives, can provide transfer environments either markedly different from, or the same as that of the initial plasma. This in turn can be expected to produce cryoprecipitated concentrates of endless variations and ratios of the myriads of native plasma constituents.

Centrifugation following thawing with the cryoprecipitate phase transfer can be carried out either as a separate process operation, as usually practiced in the prior art, or preferably simultaneously, with thawing at the selected overall temperature-time thermal drift of the processing system. Centrifugation involves a wide range of speed (RPM), gravitational force (xg), and with appropriate combinations of temperature-time schedules that must be rigidly specified especially for product standards intended for surgical or clinical use. The prior art include such variations as, for instance, unspecified cold centrifuging at 2300 xg for 10 to 15 minutes (Gestring, supra); 1000 xg for 15 minutes (Dresdale, supra); 5,000 RPM (unspecified xg) at 1° to 6° C. for 5 minutes (Siedentop, supra); and at 6500 xg for 4 minutes at +4° C. (Spotnitz, supra); in no instances of this prior art is there any indication of productivity or materials balance or appropriate qualification tests for preemptive in vitro tissue adhesion or in vivo animal testing for safe and effective tissue sealant applications.

Given the wide variations of the foregoing temperature-time schedules for each of the three process operations, the known prior art provides no cogent, discernable criteria for providing an efficient process engineering system from a source material as complex as human plasma for producing defined cryoprecipitate products by applying a novel phase transfer from plasma to a pre-prepared receiving substrate for enhanced viscosity and adhesive strength for safe and effective tissue bonding.

OBJECTIVES

To provide an improved engineering process system for producing cryoprecipitate concentrates from mammalian plasma in their native state for enhanced productivity by direct transfer into a separate pre-prepared transfer phase media comprising a solution of natural or synthetic macromolecular compounds in aqueous media for attaining enhanced viscosity and enhanced tensile break strength in living tissue bonding and sealing.

To provide an improved engineering process system for producing cryoprecipitate concentrates from mammalian plasma in their native state for enhanced productivity by direct transfer into a separate pre-prepared transfer phase media comprising a solution of natural or synthetic macromolecular compounds in sterile water, in portions of plasma, in sterile water with selected plasma entities, or in supernatants recovered from thermal drift processing.

To provide new and improved plasma cryoprecipitate concentrates supplementing or replacing in part the native plasma protein components with other natural or synthetic viscosifying compounds as substitutes for plasma proteins and polysaccharides similar or equivalent to that of native plasma and polysaccharides.

To provide a series of cryoprecipitate concentrates from recycled supernatants by similar repeated processing for a series of concentrate fractions with enhanced viscosity and tissue bonding quality.

DESCRIPTION OF THE INVENTION

These objectives are attained by applying the controlled thermal drift process engineering system from cryofreezing through the sustained solidus—liquidus equilibrium thawing transition to controlled residual icing, followed by separately or simultaneously with centrifuging as described in the original application Ser. No. 07/562,839, filed Aug. 6, 1990, now abandoned, and its continuation-in-part application Ser. No. 07/855,752, filed Mar. 23, 1992, now abandoned, related to producing native, non-denatured fibrinogen concentrates, without any chemical incursion, as described in the ensuing Examples of preferred embodiments. The process engineering system is further improved by a novel means of integral transfer of the cryoprecipitate from the plasma directly into a novel pre-prepared what is herein termed the phase transfer media comprising various aqueous solubilized supplements for producing improved plasma cryoprecipitated products in vitro and in vivo tissue bonding and sealant applications.

Phase Transfer Medium

The phase transfer medium is a pre-prepared fluid layer, in an appropriate containment such as a centrifuging tube, bottle or appropriate vessel, over which is placed the initial plasma so that the sedimenting cryoprecipitate during thawing moves by diffusion and gravitational force directly across the boundary of the plasma phase over the transfer medium and into the pre-prepared transfer medium. The pre-prepared phase medium is basically aqueous serving two specific functions, (a) for the dissolution of water soluble macromolecular supplements, natural or synthetic, serving to provide viscid or adhesive quality to the cryoprecipitate concentrates and (b) for the inclusion of selected preservatives, such as anti-coagulants, anti-fibrinolytic agents, and antibiotics, for long term shelf-life on storage.

Concentrations

The concentrations of the macromolecular supplementation in the phase transfer medium are generally in a range from about 1 to 20 percent for moderate to high molecular weights of 40,000 to 400,000 daltons, and from about 8 to 50 percent more or less for low to moderate molecular weights, from about 40,000 to about 8,000 daltons or less of the macromolecular polymer. Each molecular component in the selected transfer medium requires preliminary assessment in a progressive doubling series of concentrations, such as provided in the examples, as a means for determining the maximum concentrate for cryoprecipitate productivity consistent with optimum product qualifications. Increasing concentrations of the selected macromolecular components induces viscous resistance to transfer diffusion of the cryoprecipitate. The pre-prepared viscous media, often assisted in the case of viscous high molecular weight polymers by warming and external vortex mixing and serves as a means for incorporating preservatives and antibiotics the cryoprecipitate concentrates.

Volume Ratios. Plasma Versus Transfer Phase Media. The volume (V) proportions of starting plasma (Vp) to transfer phase (Vt), expressed as Vp:Vt, can be used in a broad range of about 20:1 to about 1:1, the latter limitation tending to over-dilute the cryoprecipitate concentrate in the transfer phase. Generally, for enhanced productivity and for specific product qualifications for tissue bonding or sealant uses the preferred range of the Vp:Vt ratio is from about 2:1 to about 40:1 and a still more preferred ratio is from about 8:1 to about 20:1.

Within these volume ratios, the optimization of the phase transfer medium for either productivity or specific product quality entails assessing each supplementing variable in the composition of the transfer phase media such as: macromolecular chemical types and ranges of molecular weights; plasma electrolytes (e.g., Ringers lactate) and low molecular weight plasma metabolites; proportionate share or ratio of the initial plasma, autologous or donor; clinical intravenous (IV) fluids; recovered centrifuged supernatants as in recycling; and antibiotics and anticoagulants. It has been discovered and demonstrated in the ensuing examples that the phase transfer of cryoprecipitates during thawing with mass diffusion across the lower plasma-transfer phase can be impeded by at least two factors: the first is that of inherent viscous resistance of the formulated medium and the second is the difference in the molecular charge or polarity of the macromolecular components interacting with that of cryoprecipitate.

Productivity

Productivity is the product of process yield multiplied by assay of the dry solids content and for uniformity and convenience stated in milligrams. The progressive concentration doubling series often reveals at low concentrations no effect on or even a decrease of productivity followed, with increasing concentrations, to a maximum and ultimately to decreased productivity of cryoprecipitate, corrected for the initial amount of the macromolecular component in the medium. Despite this sequence of decreased productivity to and from the maximum with increasing concentrations of the macromolecular components in the transfer medium, the corresponding qualification properties generally sustain the progressive increases in viscosity for viscous adhesion and for tissue bonding strength. Therefore whether to maximize productivity or some specific cryoprecipitate product quality, each of the principal variables requires a serial range of concentrations, such as by progressive doubling, usually about 3× or more as illustrated in the ensuing examples.

For productivity, the descriptive processing features in the ensuing series of Examples provide the simplest, most essential proximate assay, in terms of yield, solids contents, and the derived dry solids of productivity in milligrams, a salient feature of materials accounting or materials balance. The latter in process engineering is a requirement of technical and economic importance in ascertaining process efficiency based on the assay in milligrams of dry cryoprecipitate solids product obtained from the available milligrams of dry solids in the initial source plasma from which the cryoprecipitate is obtained. A typical human plasma lot with dry solids assay of 8.0 percent and even more, as an example, processed through the controlled thermal drift from a unit amount of 36 ml plasma makes available 2880 milligrams dry solids. From a typical cryoprecipitate thermal drift processing as described in the original application Ser. No. 07/562,839, filed Aug. 6, 1990, now abandoned, shown as a control in Example I, Table 1a, of the instant application, a cryoprecipitate concentrate yield of 1.22 grams with a dry solids content of 38.1 percent, according to the dry assay method described in the original application, amounts to the production in a single run or a single recycle of only 465 milligrams, or only 16.1 percent of available protein contents in the initial plasma. The remaining non-cryoprecipitated materials balance of 83.1 percent, actually 2415 milligrams, contains in the supernatant considerable amounts of effective and valuable tissue bonding cryoprecipitates, comprising clottable fibrinogen and residual proteins, recoverable by recycling from supernatants, generally ignored and presumably discarded in the prior art.

As indicated in the original application Ser. No 07/562,839, now abandoned, with at least two stages, Example IV, Table 4d, the recycling of the supernatant yielded substantial, as much as double the amount of the initial milligram productivity, comprising recoverable amounts of clottable fibrinogen and protein cryoprecipitates with acceptable qualifications of enhanced viscosity and tissue bonding strength. Substantial fractional supplemental milligram productivity of recycled supernatant fluids is specifically demonstrated in Example V, Table 5a Fraction series therein. This feature of enhanced productivity represents a salient contribution to the need for viral risk-free autologous fibrinogen concentrates for tissue bonding; at one time fibrinogen concentrates as fibrin sealants were commercially available from pooled human plasma sources, but banned in 1978 (FDA Drug Bulletin 8:15) and abjured clinically by medical consensus (Conte et al., New England J. Med., 309:740-4, 1983). The preparation and use of autologous fibrinogen concentrates for sealant applications has since not attained any prominence other than in the isolated instances of published prior art. Autologous source is therefore the only option but presently not of widespread utilization for reasons of prolonged preparation time, grossly inadequate productivity, and lack of defined product qualification standards.

Product Qualification

In addition to productivity and process efficiency, of equal conconitant importance are product qualifications based on standardized testing are essential to assure safe and effective use of the cryoprecipitate with regard to clinical applications, namely, with specified viscosity for viscous contact adhesion and secure tissue bonding strength.

Viscosity.

For practical purposes the simplest manner of applying the cryoprecipitate to the tissue binding site is by dispensing from a standardized syringe whereby the viscosity of the phase transfer cryoprecipitate is measured as described in application Ser. No. 07/562,839, filed Aug. 6, 1990, now abandoned, relative, that is, by comparing the force in dispensing the cryoprecipitate concentrate from a standard syringe to the force in dispensing glycerine in exactly the same shear rate and the stress dimensions; variations in the latter respects can lead to different rated viscosity values. In so dispensing the cryoprecipitate, the force (pound-force) is measured and recorded electronically, using the Instron Tensile Tester Model 1130, to maintain a steady uniform flow of about 1 ml of the cryoprecipitate concentrate extruded from a 1 ml standard 20G 1 and ½ (inch) clinical syringe at a constant displacement forcing speed of one inch per second. For instance, comparing the 7.40 pound-force for dispensing glycerine as a reference standard with a viscosity of 1150 centipoises, the 0.936 pound-force expended with a typical cryoprecipitate concentrate, 29.7 percent solids, amounts to a viscosity of 155 centipoises relative to glycerine, that is, proportionately to the force expended in dispensing glycerine with the same syringe; syringes from different manufacturers and with allowable bore tolerances can be expected to reflect as much as 12 percent differences in expended force calculated as relative to that of a similarly dispensed glycerine standard. The pound-force units in the range of few pounds more or less is more commonly sensed to the touch and understood in syringe dispensing compared to equivalent gram force. The chart recorded pound-force also provides a useful and informative time-dependent profile as a sequence of the smoothness of the syringe-dispensed flow, in turn expressed in terms of the percent standard deviation of the recorded pound-force averaged from a sequence of from about six to eight readings of the continuous syringe extrusion profile.

The relative viscosity and smoothness profile, usually in the range of about 92 to 98 percent, as in the case of the glycerine standard, provides a useful and important criteria of initial product homogeneity and also their measured changes on prolonged storage for product stability based on attendant incipient nucleation or gross coagulation or other macromolecular transformations. Glycerine is a preferred choice as a viscous reference, often stated as a standard having in common the viscous adhesion or tenacity comparable to that of cryoprecipitated concentrates phase transferred into pre-prepared viscous media.

The evaluation of the viscous enhancement with natural occurring and synthetic macromolecular supplementation of the cryoprecipitate concentrates is based on comparisons with cryoprecipitates prepared without the intervening phase transfer as controls. The controls at approximately equivalent solids content of about 36 percent solids are rated at about 80 centipoises relative to that of the glycerine standard. The viscous enhancement beginning at about 90 to 100 centipoises with the macromolecular, natural or synthetic, supplementation in the transfer phase can be attained either by progressive increases in the concentration or by progressive increases in molecular weight of the macromolecular supplementation with corresponding increases in in vitro bonding strengths. For syringe dispensing, the viscosity beyond about 800 centipoises is about the limit for steady prehensile forcing, and may be further limited to about 400 centipoises with decreasing productivity due to increasing resistance to diffusion of the cryoprecipitate into the viscous transfer phase. These limitations can be expected to decrease or increase during the progressive, as fractional, designated as Fractions, depletion of the cryoprecipitate from the plasma and depending upon the ever changing multitudinous and complex intermolecular and interphase forces.

Bonding Strength

Following the product viscosity qualifications in terms of relative viscosity and its smoothness profile, the ensuing in vitro chamois tissue bonding is determined in terms of tensile break force of the cryoprecipitate applied edge-wise to the separated edges of an incision with appropriate activation, either with thrombin or by spectral absorption, as described in application Ser. No. 07/562,839, now abandoned, by testing on the Instron Tensile Tester, Model 1130, for the measured tensile break strength in terms of pound force (lb-f) per inch of width (in-w). The test method is based on ASTM Designation D-638-68 Method prescribed by the American Society for Testing and Materials as adapted to the ensuing description with in vitro test bonded described chamois.

The bonding involves re-joining incised, half-inch wide strips of clean chamois cut in the mid-section three-inch lengths to which a thin layer of the cryoprecipitate is applied from the syringe contents. The bonding is accomplished by any one of the several phenomenon physical, chemical, mechanical mechanisms, and combinations thereof. These include passive, direct viscous cohesive or adhesive contact within minutes or by spectral or thermal absorption and by thermal activation within seconds or by thrombin-calcium chloride activation in a matter of minutes to an hour or so; often the latter is referred as passive bonding intended to distinguish from bonding by external application or exposure to absorptive spectral energy of laser and ultra-violet or with microwave absorption. By passive adhesion is meant inherent or intrinsic adhesion as in the case of simple glues by cohesion or adhesion or by combination thereof to a minimum specified bonding strength. By spectrally activated bonding is meant the bonding attained by the use of applied energy resulting from intermolecular anhydration or dehydration induced by microwave, laser, or ultraviolet at selected frequencies supplementing the initial passive adhesion by the inherent viscous tenacity or tack.

The relatively inexpensive in vitro chamois tissue bonding with standardized chamois strip tensile break test serves as a product qualification test and thereby eliminates or decreases dependence on the highly expensive, extended in vivo animal tests. The bonding can therefore be specified to a minimum bonding tensile break strength of at least 1.0 pound-force and preferably 2.0 pound-force or higher per incision bonding width of one inch. As made evident in the ensuing examples, this minimum qualification is achieved and enhanced substantially by the novel phase transfer process compared to cryoprecipitates produced without straight non-phased controls.

The process features of the two inventions, the first application Ser. No. 07/562,839, now abandoned, relating to controlled thermal drift process, and the herein second application relating to innovative phase transition provide the essential processing specifications of cryofreezing, thawing and centrifugation operations for enhanced productivity integrally related to enhanced in vitro product specifications. In effect, the process specifications of the instant applications are in fact part of the product specifications. As herein described the essential product specifications in turn include viscosity and the in vitro bonding of tissue derived from animal source such as the chamois as a bonding qualification test for in vivo animal tissue application.

The ensuing Examples provide a series of preferred embodiments of this invention serving to supplement the native cryoprecipitated plasma proteins with natural polysaccharides and with substantially equivalent synthetic or synthetically modified polysaccharide configurations found to be uniquely effective in modifying or moderating the viscous and adhesive properties of cryoprecipitated plasma protein products for use in tissue adhesive and bonding.

EXAMPLE I

This example of a preferred embodiment describes the manner in which native cryoprecipitates are transferred from plasma or serum phase by means of applied force of centrifugal sedimentation into a layered phase of viscous solutions of high molecular weight polysaccharides serving to supplement and improve the viscous and adhesive properties of the cryoprecipitated concentrates. This example uses a naturally occurring pectin or pectic acid as a typical polysaccharide chemically known as methylated polygalacturonic acid, existing in a broad molecular weight range from about 20,000 to 400,000 about daltons, a range approximating that of cryoprecipitated fibrinogen concentrates more or less. In this example the naturally occurring grades of (a) polygalacturonic and (b) the corresponding more soluble potassium salt are used to illustrate their respective enhancement of process productivity.

Polygalacturonic acid (pectin)

The purpose of this first part of Example I is to ascertain the effect of the macromolecular weight component of the viscous phase transfer media on the productivity and cryoprecipitate assay using such physiological media as (a) plasma transfer phase with its full range of primordial electrolytes and native organic constituents replaced by (b) Ringer's lactate, and (c) sterile water excluding physiological constituents. Polygalacturonic acid, known generally as pectin, is a prominent plant source type of polysaccharide with a range of molecular weights from about 20,000 to about 400,000 which approximates the range of the proteins and glycoproteins of human plasma extending from albumins to fibrinogen.

A freshly prepared 10 percent solution of a commercially available pectin (Sigma Chemical Company, either P 2157 or P 9153), is prepared using 6.25 grams moistened with a drop glycerine dispersed separately in 62.5 ml volumes of human plasma, in Ringer's lactate, and in sterile water in a wide-mouth capped bottle (Gibco 150 ml serum bottles) and stirred vigorously over a warming plate to 45° C. until uniformly dissolved or dispersed to a slightly gelatinous, highly viscous transfer phase with a slight haze. This high molecular grade of pectin, often classified as a hydrocolloid, was selected to ascertain the extent to which viscosity would impede the diffusion of cryoprecipitate into the transfer media.

Four milliliters (ml) of each of the three 10 percent viscous media are placed in sterile 40 ml polypropylene centrifuge tubes (Du Pont 130×15 mm) to serve as separate, bottom layer transfer phase over which the plasma cryoprecipitates transfers during centrifugal sedimenting from the thawing cryofrozen plasma. Aliquot 36 ml portions of human plasma, thawed from −20° C. storage, are poured over the bottom transfer phase in the polypropylene tubes and the tubes then capped with a sterile polypropylene stopper. The volumes of the two phases in this example, namely, 36 ml of the initial plasma to 4 ml of the transfer medium, correspond to a ratio of 9:1 which is an essential process specification relating to productivity and to quality characteristics of the resulting cryoprecipitate products applicable to a broad range from about 1:1 or less to about 40:1 or more.

The two layer phases, the upper plasma over the lower transfer phase, are processed for phase transfer cryoprecipitation according to the thermal drift process described in preceding patent applications, Ser. No. 07/562,839, filed Aug. 6, 1990, now abandoned, and Ser. No. 07/855,752, filed Mar. 23, 1992, now abandoned, with the sequence of processing steps specified in Table 1a for a non-phase control and three different transfer phase media. In this Example as in the succeeding examples the effects of the specified process engineering variables of temperature, time and centrifuge force (xg) are expressly specified from the residual icing, item (a), to the preferred range from about 5 percent to about 95 percent. The latter serves to control and sustain the solidus—liquidus equilibrium and to restrict the transition to complete liquidus state beyond which the continued dissolution of cryoprecipitates into the supernatant phase would incur significant losses of the valuable native plasma macromolecular components known as mucopolysaccharides and mucoproteins.

On completion of the centrifuging operation, the clear upper phase supernatant plasma with the elevated solid ice plug is decanted from the lower phase of sedimented cryoprecipitate usually designated as Fraction I and the supernatant plasma recombinant with the recovered thawed ice plug are set aside for further recycling serially into a sequence of re-cycled Fractions from the decanted supernatant layer.

Table 1a summarizes the effects of the different transfer phase media and the non-phase control on the productivity based on the corresponding resulting yield, listed as item (b) and solids (dry) assay item (c) from which the productivity in milligrams item (d) of cryoprecipitated concentrates is derived for the materials balance of this example.

TABLE 1a

Enhanced Human Plasma Cryoprecipitate Productivity
Phase Transfer into Polygalacturonic Acid Media Cryofreezing: −80° C. 1 hour
Thawing: simultaneous with centrifuging
Centrifugation: +10° C. 64 min. 8000 xg
Unit process volume: 40 ml (36 ml plasma)
Phase transfer volume: 4 ml, 10% stock solution, (400 mgm)
Initial plasma solids: 8.00 percent (2880 mgm/36 ml)

| Phase Transfer Medium | Rsdl Icing (%) (a) | Yld Conc (g) (b) | Slds Asy (%) (c) | Productivity solids content* (mg) (d) | Productivity solids content* (%) (e) | (f) | Enhncd Cntrl* Ratio (g) |
|---|---|---|---|---|---|---|---|
| Cntrl** | 30 | 1.22 | 38.1 | 465 | — | 14.5 | — |
| Plasma | 60 | 16.9 | 12.6 | 2134 | (1734) | 60.2 | (3.72) |
| Ringers Solution | 50 | 14.2 | 13.1 | 1680 | (1280) | 44.4 | (2.75) |
| Water | 50 | 23.1 | 11.3 | 2608 | (2408) | 83.6 | (5.18) |

*Productivity and enhancement ratio corrected for 400 mgm of polygalacturonic acid added separately initially in the various transfer media.
**Without phase transfer medium applying the controlled thermal drift processing system of Application Serial No. 07/562,839, now abandoned.
Cntrl = Control, Rsdl = Residual, Yld = Yield, Slds Asy = Solids Assay.

Materials Balance

Based on the initial unit plasma volume, 36 or 40 ml, as the case may be, of the initial assay of dry plasma of solids of 8.00 percent, the available dry solids calculates to 2880 milligrams as the basis for comparing the enhancement of productivity in this example the control without the transfer phase provides 465 milligrams of solids content comprising 288 milligrams of clottable fibrinogen and milligrams of residual associated protein based on the assay test method described in preceding application Ser. No. 07/855,752, filed Mar. 23, 1992, now abandoned.

In the case of the phase transfer process using the three different medium with 10 percent pectin (polygalacturonic acid), the rated productivity transfer is enhanced substantially over the 465 milligrams of dry solids attained with the non-phase control. Corrected for the 400 mgm of pectin in the transfer media, the quantitative productivity, item (e), as indicated in Table 1a, is significantly different with the increasing order of: Ringers lactate (1280 mgm), plasma (1734 mgm), and sterile water (2208 mgm) and of the same order with percent productivity item, (f), and enhancement ratio (g) compared to the control.

On this account, the sterile water is most frequently used in ensuing examples but with no exclusion of the other two media types that can be expected to provide some selectivity of constituent diffusion into the transfer phase. The broad range of productivity among the three different phase media is believed attributable to the chemical variability of the transfer phase with regard to electrolyte charge, molarity, and viscosity. In the case of pectin in the sterile water transfer phase, the productivity is enhanced 5.61-fold or 4.75-fold when corrected for the added 400 mgm of pectin polysaccharide. Similarly, replacing the sterile water by Ringers lactate and by plasma for dissolution of the pectin enhances the productivity 4.00-fold (3.14 corrected) and 4.59-fold (3.73 corrected), respectively. In terms of the attained dry solids content, item (d) in Table 1a divided by 2880 initial plasma solids, the transfer phase with the series of three different media removed 86.3, 44.7, and 60.2 percent initial plasma solids, compared with only 16.1 percent with the non-phase control; the latter corresponds to high, 83.9 percent balance of plasma solids remaining in the spent plasma supernatant as mucopolysaccharides and mucoproteins of potential value for tissue adhesives and sealants. It is on this unexpected and surprising discovery that the valuable merits of phase transition with recycling of useful products have been made evident in this invention not only for productivity but also for highly effective in vitro and in vivo tissue bonding applications demonstrated in ensuing Examples.

Potassium Polygalacturonate. The potassium salt of pectic acid provides the potential merit of a more readily dissolvable form of pectic acid and in its ionic state and mass anionic charge for interaction with native plasma proteins using a broad, progressive concentrations range below and above the 10 percent concentration used in the preceding example of cryoprecipitation, transfer phase with pectin as polygalacturonic acid.

As in the preceding pectin example, a progressive series of doubling phase transfer concentrations from 0.05 to 0.40 gram (0.13 to 1.05 percent concentration) of potassium polygalacturonate (Sigma Chemical Company, product P 7276) dissolved in 2 ml sterile water is placed as lower phase layer in quadruplicate set of polypropylene tubes. Over the contents of each tube, four aliquots of 38 ml of human plasma, thawed from frozen storage state, are poured as upper phase layer; in this case, the ratio of the initial plasma volume to that of the phase volume is rated at 19:1. The capped contents are then cryofrozen at −80° C. for one hour followed by simultaneous thawing and centrifugation at +10° C. for 64 minutes at 8000 xg. Following the completion of centrifugation the supernatant is carefully drained off from which the solid ice plug weighed for percent residual icing.

As summarized in Table 1b the productivity in terms of dry solids content in milligrams, item (d), is evident at as low as 2.5 percent transfer phase concentration increasing progressively up to a maximum around 10 percent beyond which a significant decrease in productivity is evident but still significantly higher than that of the non-phase control, both actual and corrected for the added potassium polygalacturonate. Compared with the productivity indicated in Table 1a, it is seen in the progressive series that above the 10 percent concentration of the anionic potassium polygalacturonate the productivity in milligrams, item (d), begins to decline as does the enhancement ratio over the control, item (g), corrected for amount of the potassium polygalacturonate added to the phase transfer medium. It is evident that increasing concentrations imposes significant molecular resistance to the diffusion of the plasma cryoprecipitates across the phase transfer boundary into the phase transfer medium under the limitations of the specific processing conditions of this example.

EXAMPLE II

Naturally occurring polysaccharides include numerous subsidiary variants structured predominantly not only from a single pyranose repeat unit, such as the preceding polygalacturonic acid, but also from chemically different paired units. A biologically prominent example of the latter is hyaluronic acid, an anionic macromolecular mucopolysaccharide with alternating, paired glucuronidic and glucosamidic repeat units comprising a relative low molecular polymeric configuration with a molecular weight in the range of 50,000 daltons. A series of progressive doubling concentrations from 0.02 to 0.16 gram (0.67 to 5.34 percent) in 3 ml of sterile water is repeated, as described in the preceding Example using potassium polygalacturonate, for phase transfer from 37 ml of human plasma; the volumes of the two phases in this example correspond to a ratio of 12.3:1.

TABLE 1b

Enhanced Human Plasma Cryoprecipitate Productivity
Phase Transfer into Potassium Polygalacturonate Media Cryofreezing: −80° C. 1 hr.
Thawing: simultaneous with centrifugation
Centrifugation: +10° C. 64 min. 8000 xg
Unit plasma volume: 40 ml (38 ml plasma)
Phase transfer volume: 2 ml
Initial plasma solids: 8.00 percent (2880 mgm/36 ml)

| Potassium Glucuronate (g) | (%) | Rsdl Icng (%) (a) | Yld (g) (b) | Slds assay % (c) | Dry Solids content (mg) (d) | (e) | Enhancement (corrected)* ratio (f) | (g) |
|---|---|---|---|---|---|---|---|---|
| 0 (control)** | | 30 | 1.22 | 38.1 | 465 | — | — | — |
| 0.050 | 2.5 | 90 | 1.63 | 34.4 | 571 | (521) | 1.23 | (1.12) |
| 0.10 | 5.0 | 90 | 2.23 | 31.9 | 711 | (611) | 1.53 | (1.31) |
| 0.20 | 10.0 | 90 | 3.28 | 32.8 | 1076 | (876) | 2.31 | (1.88) |
| 0.40 | 20.0 | 90 | 2.73 | 35.1 | 958 | (558) | 2.06 | (1.20) |

*Parenthetical ratios correcting for the progressive series of potassium polygalacturonate, in milligrams, added initially in the phase transfer medium.
**Without phase transfer media applying the control thermal drift processing system.
Rsdl Icng = residual icing, Yld = yield.

As indicated in Table 2a, the molecular weight grade of this source of hyaluronic acid requires a concentration level in the phase transfer of at least about 2.67 percent to attain significant increase in productivity of dry solids in milligrams, item (d), over that of the control with an enhancement ratio 1.31 or 1.14 when corrected for the initial hyaluronic acid in the phase transfer medium. Above the 2.67 percent concentration a significant decline in productivity ensues owing to increased resistance to the diffusional transport due to increased viscosity but, as indicated in Table 2b, with sustained increase in bonding tensile break strength despite the decline in productivity. This example, with the specified thermal conditions and the chemical constituency of the selected transfer medium, indicates that other, broadened variants in molecular weights and in the biological sources of hyaluronic acid can be used to produce cryoprecipitates directed to optimized protein constituency for in vivo bonding or sealing in specific types of tissue variants, such as skin, arteries, nerves, ophthmalogical, etc.

Accordingly, the minimal enhancements indicated in this example can be expected to attain considerably higher productivity and enhancement ratios with other higher or lower molecular weight grades of hyaluronic acid and by increasing concentrations up to about 20 percent in the phase transfer medium. Moreover as regards to the adjustments in process variables, reducing the simultaneous thawing and centrifuging time of 64 minutes resulting in 30 percent residual icing, item (a) in Table 2a, to 32 minutes as in Table 1b item (a) to higher residual of 90 percent icing provides significantly higher productivity compared to the non-phase transfer controls.

TABLE 2a

Enhanced Human Plasma Cryoprecipitate Productivity
Phase Transfer into Hyaluronic Acid Cryofreezing: −80° C. 1 hour
Thawing: simultaneous with centrifuging
Centrifugation: +10° C. 64 min. 8000 xg
Unit process volume: 40 ml (37 ml plasma)
Phase transfer volume: 3 ml sterile water solution
Initial plasma solids: 8.00 percent (2960 mgm/37 ml)

| Hyaluronic acid (transfer phase) | | Rsd Icn | Yld | Slds Asay | Dry Solids Content | | Enhancement (corrected)* ratio | |
|---|---|---|---|---|---|---|---|---|
| (g) | (%) | % (a) | (g) (b) | % (c) | (mg) (d) | (e) | (f) | (g) |
| 0 (control)** | | 30 | 1.22 | 38.1 | 465 | — | — | — |
| 0.02 | 0.67 | 30 | 1.20 | 35.9 | 431 | (429) | 0.93 | (0.92) |
| 0.04 | 1.33 | 30 | 1.38 | 35.4 | 489 | (449) | 1.05 | (0.97) |
| 0.08 | 2.67 | 30 | 1.69 | 36.0 | 608 | (528) | 1.31 | (1.14) |
| 0.16 | 5.34 | 30 | 1.85 | 35.0 | 648 | (488) | 1.39 | (1.05) |

*Parenthetic ratios correcting for the 400 milligrams (1.11 percent plasma supplementation) of hyaluronic acid added initially to the various phase transfer media.
**Without phase transfer media.
Rsd Icn = Residual Icing, Yld = yield

TABLE 2b

Enhanced Human Plasma Cryoprecipitate Productivity
(Continued from Table 2a)
Effect on Viscosity and In Vitro Adhesion Strength

| Hyaluronic Acid (phase transfer) | | Viscosity relative (glycerol stnd)* | Bonding strength (chamois test - MW)** |
|---|---|---|---|
| (g) | (%) | centipoises, av. | lb-f/in, av. |
| 0 (control)*** | | 83 | 3.54 |
| 0.02 | 0.67 | 79 | 3.21 |
| 0.04 | 1.33 | 81 | 3.77 |
| 0.08 | 2.67 | 101 | 3.94 |
| 0.16 | 5.38 | 126 | 4.97 |

*Applied force (lb-f) at 2 in/min through 1 ml syringe with AWG 20 1¼ needle.
**MW - microwave exposure, maximum strength at 2 to 8 seconds.
***Without phase transfer media.

EXAMPLE III

This example utilizes a chondroitin sulfate, a naturally occurring mucopolysaccharide comprising repeating units of N-acetyl-chondrosine with one sulfate group per disaccharide unit reminiscent of the unmodified cellobiose units of cellulose and prominent as a biological matrix in skeletal and soft connective tissue, thus providing an important augmentation in the role of plasma derived tissue sealants. The natural occurring biological chondroitin sulfate in this example is used in transfer medium of human plasma thereby providing a complete plasma homogeneous system compared to the preceding heterogenous systems with synthetic macromolecular supplementation in aqueous transfer medium.

A progressive doubling series of phase transfer media is prepared with 0.05, 0.10, 0.20, and 0.40 gram of sodium chondroitin sulfate A, Sigma Chemical Company, Product C 8528, estimated at a molecular weight of 50,000 daltons, dissolved in 3 ml portions of the plasma from which the cryoprecipitate is to be produced, in 40-ml polypropylene centrifuge tube, to which is added 0.9 ml of Kefzol (Lilly) cefazolin sodium antibiotic solution with vortexing followed by 35 ml of freshly warmed plasma from frozen storage followed by 35 ml of plasma phase superimposed carefully over the phase transfer media; the volumes of the two phases in this example, namely 35 ml of the initial plasma to 3 ml of the phase transfer medium, corresponds to a ratio of 11.7. The capped polypropylene contents are cryofrozen at −80° C. for one hour and then centrifuged with simultaneous thawing in the Du Pont RC-5C Superspeed Centrifuge pre-set to +10° C. for controlled deicing in the solidus—liquidus transition equilibrium for 32 minutes at 8000 xg; an identical separate control run with 38 ml the same plasma is made without the pre-prepared phase transfer media. The residual ice, usually as a solid plug, and the supernatant fluid are decanted and saved for further recycling from repeated cryofreezing into one or more fractions of cryoprecipitates. The sedimented cryoprecipitates are then assayed for materials balance on productivity and for product qualifications in terms of viscosity relative viscosity, and in vitro tissue bonding strength.

Table 3a summarizes the process details relative to productivity in terms of the dry solids contents, item (d), of the progressive concentration doubling series of chondroitin sulfate ranging from 1.67 to 13.3 percent. The maximum dry solids milligram productivity, corrected for the added polysaccharide, is attained at the lowest concentration of 1.67 percent and then gradually decreases as shown in Table 3a with regard to the cryoprecipitate dry solids content and particularly the enhancement ratio resulting presumably from increasing resistance to the diffusion of the plasma cryoprecipitate into the transfer phase.

On the other hand, as shown in Table 3b, the effect of transfer phase concentration on the qualification properties indicates a consistent progressive increase in relative viscosity commencing at 3.33 percent supplementation of chondroitin sulfate and in the case of the in vitro tensile break strength commencing at 6.67 percent supplementation with the biological occurring macromolecular chondroitin sulfate. This example provides the basis for further enhancement of productivity and tissue bonding strengths with other possible variants of the process engineering steps and compositions including other phase transfer media such as portions of the initial plasma, recovered supernatants, clinical sera, etc., such as used in Example I, Table 1a.

TABLE 3a

Enhanced Human Plasma Cryoprecipitate Productivity
Phase Transfer into Chondroitin Sulfate Polysaccharide Cryofreezing: −80° C. 1 hour
Thawing: simultaneous with centrifuging
Centrifugation: +10° C. 64 min. 8000 xg
Unit process volume: 35 ml
Phase transfer volume: 3 ml plasma
Initial plasma solids: 8.00 percent (2960 mgm/35 ml)

| Chondroitin Sulfate | | Rsd Icn | Yld | Slds Asay | Dry Solids Content | | Enhancement (corrected)* ratio | |
|---|---|---|---|---|---|---|---|---|
| (g) | (%) | % (a) | (g) (b) | % (c) | mg (d) | (e) | (f) | (g) |
| 0 (control)** | | 30 | 1.22 | 38.1 | 465 | — | — | — |
| 0.05 | 1.67 | 25 | 2.03 | 31.9 | 649 | (599) | 1.40 | (1.29) |
| 0.1 | 3.33 | 25 | 1.93 | 30.2 | 583 | (483) | 1.25 | (1.04) |
| 0.2 | 6.67 | 25 | 1.83 | 30.1 | 550 | (350) | 1.18 | (0.75) |
| 0.4 | 13.3 | 25 | 2.03 | 29.7 | 603 | (203) | 1.30 | (0.44) |

*Parenthetical ratios correcting for the progressive series of chondroitin sulfate, in milligrams, added initially in the phase transfer media.
**Without phase transfer media.
Rsd Icn = Residual Icing, Yld = Yield, Slds Asay = Solids Assay TABLE 3b Enhanced Human Plasma Cryoprecipitate Productivity
(Continued from Table 3a)
Effect on Viscosity and In Vitro Bonding Strength

| Chondroitin sulfate (phase transfer) | | Viscosity relative (glycerol stnd)* | Bonding strength (chamois test - MW) |
|---|---|---|---|
| (g) | (%) | centipoises, av. | lb-f/in, av. |
| 0 (control)** | | 83 | 3.54 |
| 0.02 | 1.67 | 82 | 3.72 |
| 0.04 | 3.33 | 102 | 3.44 |
| 0.08 | 6.67 | 113 | 4.39 |
| 0.16 | 13.3 | 145 | 5.51 |

*Applied force (lb-f) at 2 in/min through 1 ml syringe with 1¼ AWG needle.
**Without phase transfer media.

EXAMPLE IV

In this example a water soluble modified macromolecular polymer, sodium carboxymethylcellulose is used as preferred embodiment substituting for or Supplementing biological and natural occurring macromolecular polymers. As in the preceding example like the catonic chondroitin sulfate polysaccharide, the anionic chemically modified sodium carboxymethylcellulose is used to demonstrate the use of natural and synthetic gums for their visco-elastic properties as component constituents of native cryoprecipitated plasma proteins for in vitro and in vivo animal tissue bonding applications.

Sodium carboxymethylcellulose (CMC-Na), low-medium viscosity grade (Du Pont P-125) is added in progressive doubling amounts of 0.50, 0.10, 0.20, and 0.40 gram, dissolved in a transfer phase medium of 2 ml sterile water in a 40-ml polypropylene centrifuge tube, to which is added 0.90 ml of Kefzol (Lilly) cefazolin sodium antibiotic solution with vortexing followed by 38 ml of freshly warmed plasma from frozen storage superimposed carefully over the phase transfer media; in this case the volume of the initial plasma to that of the transfer phase medium is 19:1. The capped polypropylene tube contents are cryofrozen at −80° C. for one hour and then centrifuged with simultaneous thawing for 32 minutes at 8000 xg in the Du Pont RC-5C Superspeed Centrifuge pre-set to +10° C. for controlled de-icing in the solidus—liquidus transition equilibrium; an identical separate control run with 38 ml the same plasma is made without the pre-prepared phase transfer media. Following the completion of the centrifuging, the residual ice plug is removed and measured for volume percentage of the initial plasma volume and recombined with the decanted supernatant fluid for further recycling from repeated cryofreezing into one or more fractions of cryoprecipitates. The progressive series of sedimented cryoprecipitates are then assayed for productivity and for product qualifications in terms of viscosity, relative viscosity and in vitro and in vivo tissue bonding strength.

Productivity

Table 4a summarizes the productivity of the progressive series of CMC-Na concentrations commencing in the phase transfer medium with initially a decrease in dry solids content at 5.0 percent and gradually increasing to significant enhancement ratio over the control by a product ratio of 5.70 or 4.77 when corrected for the 400 milligrams included in the initial transfer medium. The phase transfer medium expanded to a visibly viscid layer of the thawed cryoprecipitate, presumably due to inhibition of water from the plasma forming a gelatinous phase intermediate to that of the initial transfer medium and the supernatant phase with the formed ice plug.

In this example using CMC-Na, the maximum productivity, corrected for the attained cryoprecipitates less the added macromolecular component in the transport phase, is attained at the 20 percent concentration. As indicated in the examples of this application, the maximum productivity concentration was evident with as low as 1.67 percent with macromolecular components of different chemical, ionic and non-ionic, types and ranges of molecular weights; in the latter respect, the range of concentrations in the transfer media from 1.67 concentration, with chondroitin sulfate, to 20 percent concentration, with CMC-Na, can be still further broadened from about one percent or less to about 20 percent or more for some specific or selected product assay maximum. Moreover, maximum productivity for a selected cryoprecipitate assay of the solids content can be attained by adjusting the volume ratios of the initial plasma to the transfer medium from as low as 9:1, such as used with polygalacturonic acid and its corresponding potassium compound, to as high as 30:1 with hyaluronic acid and an intermediate ratio of 19:1 with CMC-Na macromolecular components in the transfer media. The range of the initial plasma volume to the phase transfer volume ratio can be broadened from about 1:1 or less to about 40:1 for production of specific plasma components of the multitudinous native protein entities with a broad macromolecular concentration range in the phase transfer. Further and thirdly with an applied range of combinations of the thermal drift profile, notably the percent residual icing, a three-dimensional set of ranges provides for a process and product system for the production of specific maximized plasma entities, such as native hematological factors, cell growth factors, and so on prepared otherwise by expensive and low-yielding immunogenic, chemically absorptive, and chromatographic means.

TABLE 4a

Enhanced Human Plasma Cryoprecipitate Productivity
Phase Transfer into Sodium Carboxymethylcellulose Media Cryofreezing: −80° C. 1 hour
Thawing: simultaneous with centrifuging
Centrifugation: +10° C. 32 minutes 8,000 xg
Unit process volume: 38 ml plasma
Phase transfer volume: 2 ml sterile water
Initial plasma solids: 8.1 (av.) percent (8100 mgm/100 ml)

| Carboxymethyl cellulose, sodium | | Rsd Icn | Yld | Slds Asay | Dry Solids Content | | Enhancement (corrected)* ratio | |
|---|---|---|---|---|---|---|---|---|
| (g) | (%) | % (a) | (g) (b) | % (c) | mg (d) | (e) | (f) | (g) |
| 0 (control)** | | 30 | 1.22 | 38.1 | 465 | — | — | — |
| 0.05 | 2.5 | 25 | 1.19 | 31.1 | 394 | (344) | 0.85 | (0.74) |
| 0.1 | 5.0 | 30 | 2.34 | 25.2 | 590 | (490) | 1.36 | (1.13) |
| 0.2 | 10.0 | 30 | 3.85 | 17.1 | 658 | (458) | 1.52 | (1.06) |
| 0.4 | 20.0 | 30 | 12.58 | 19.6 | 2466 | (206) | 5.70 | (4.77) |

*Parenthetical ratios correcting for the progressive series of CMC-NA added to media.
**Without phase transfer media.
Rsd Icn = Residual Icing, Yld = Yield, Slds Asay = Solids Assay.

Product Qualification

Table 4b summarizes the qualification tests of the progressive doubling series of 3-fold (3×) CMC-Na concentrations in a phase transfer medium of sterile water. In this series the increase in the viscosity of the cryoprecipitated concentrate commences at about 5.0 percent concentration of the CMC-Na in the transfer phase medium attaining substantial enhancement at 20 percent concentration. In the case of the in vitro chamois bonding strength in terms of measured tensile break force, the increase commences progressively from about 2.5 percent concentration to substantial enhancement at 20 percent. On the basis of the combination of substantial productivity along with the attained enhancement in viscosity and the in vitro tensile break force, the 20 percent CMC-Na concentration with the 19:1 ratio of the initial plasma to the aqueous phase transfer medium supplemented, with heretofore indicated preservatives and antibiotics, has been used successfully in extended in vivo animal testing to complete healing of bonded incisions.

The aqueous transfer medium using sterile water for the CMC-Na supplementation can be replaced with conventional clinical serum and with other plasma byproduct sera with significant enhancement of the viscosity and an improved syringe flow. The CMC-Na can be replaced by other macromolecular supplementation in phase transfer described in this example and has also been applied successfully to such other mammalian bovine and porcine plasma with substantially equivalent productivity and product qualification.

TABLE 4b

Enhanced Human Plasma Cryoprecipitate Productivity
(Continued from Table 4a)
Effect on Viscosity and Tissue Bonding Strength

| CMC-NA (phase transfer) grams % | Viscosity, relative. (glycerol standard)* centipoises (ratio)*** | | Bonding strength (chamois test)** lb-f/in-w (ratio)*** | |
|---|---|---|---|---|
| 0 (control)**** | | 83 (reference) | 3.54 | (reference) |
| 0.05 | 2.5 | 84 | 1.01 | 4.24 | 1.20 |
| 0.1 | 5.0 | 98 | 1.18 | 4.22 | 1.19 |
| 0.2 | 10.0 | 112 | 1.35 | 5.89 | 1.66 |
| 0.4 | 20.0 | 218 | 2.63 | 7.67 | 2.17 |

*Applied force (lb-f) at 1 in/sec through 1 ml syringe with 1½ AWG needle.
**Microwave bonding, maximum in the 2 to 8 seconds range.
***Enhancement over control.
****Without phase transfer.

Storage stability

The foregoing in vitro qualification tests utilized cryoprecipitate concentrates formulated with Kefzol antibiotic and 0.02 to 0.32 gram, preferably and adequately with 0.04 gram, of epsilon-amino-n-caproic acid (EACA) stabilizer added directly into the initial phase transfer medium, either before or after processing, in order to attain reasonable shelf life on prolonged refrigerated storage at 0° to 4° C.; EACA is a synthetic replacement for polypeptide inactivators such as aprotinin for stabilization in long term storage. Cryoprecipitates produced from 42 different lots of human plasma stored up to 327 days at 0° to +4° C. refrigeration were still useful and effective for both the in vitro qualification and the in vivo incised skin tissue bonding. Such stabilized concentrates during storage showed increases and decreases in the measured syringed viscosity in range of about 18 to 24 percent changes from the freshly prepared concentrates. This is presumably due to fibrinogen polymerization of varying degrees of clotting, on the one hand, and decreases due to fibrinolysis on the other. During long term storage both mechanisms with over-balance of either the polymerization or the lysis would be reflected by the viscosity changes on storage; incipient unusable clotting resulted in only two of the 42 lots of cryoprecipitates of undetermined causes or some inherent variability of initial quality of the mammalian plasma.

In vivo animal tissue bonding. As described in application Ser. No. 07/855,752, now abandoned, the phase transfer cryoprecipitate concentrate of this Example produced with 0.40 gram CMC-Na in 2 ml sterile water transfer medium is used as a replacement for and comparison with conventional suturing in closing skin incisions serving as a model for all other physiological tissue bonding and sealant applications.

A 50/50 admixture of the cryoprecipitate with a fresh stock of 15 NIH units of thrombin in 20 microliters of 0.5 mM calcium chloride is applied from a standard 20G 1½ 1 ml clinical syringe, the same as used for syringe viscosity specification measurements, is applied along either edge of a 6 centimeter length incision made on the dorsal skin of Wistar rats 2 to 3 centimeters distant from and parallel to the spine. The adhesive contact is made secure by stretching lightly for about a minute lengthwise from both ends of the rejoined edges of the incision to make firm, pressured contact of the continuous, syringed beading of the cryoprecipitate applied along either one or both of the incision edges. A single midline suture across the 6 cm length of the incision is provided as a safeguard to maintain a straight line stable contact bonding during the early, critical 7 to 14 day period of the 90-day extended healing period, against the constant straining motions of the active rat during entire healing period.

Starting from the fourth day, retrieved quadruplicate specimens from euthanized rats were sectioned into ½ inch widths across the healed incision midway between 6 centimeter in lengths. The cut specimens were tested immediately in complete immersion in Ringers lactate or in saline solution between test grips one inch apart for a complete stress strain profile recorded by the Instron Tensile Tester for all the conventional tensile constants. These include initial modulus, break force and elongation to break in accordance with modified dimensions of ASTM Designation D 638-1968 version at grip speed C of 2 inches per minute; the grip speed stretching is of paramount importance, as are also test dimensions, for all the stated tensile constants including the practical tensile break force. Each test specimen is measured for incision thickness which with the test width provides the cross section area for converting the tensile break force to normalized tensile stress or strength; the thickness of healed rat tissue and the non-incised controls ranged from approximately 0.072 to 0.092 inch, from which the corresponding tensile stress (lb/sq in) values are derived from each Instron recorded stress-strain, often referred to as the force-elongation profile, from which the ensuing tensile break strength as pound-force values are averaged from quadruplicate retrieved specimens.

Table 4c summarizes the tensile break force (strength) data of the extended 90-day progressive rat tissue healing of retrieved incision specimens comparing the tensile break force of the thrombin activated cryoprecipitate bonding, item (b), with that of suturing, item (c), along with corresponding tissue regain of the tensile break force to that of the normal control tissue (a). At 90 days the cryoprecipitate bonded by thrombin-calcium chloride attains substantial, 96.7 percent regain of that of normal non-incised control compared to a considerably lower regain of 62.5 percent with suturing. This means that from an extrapolation of the long term retrieval data the sutured healing would take about 24 days to attain the tissue regain equivalent to that of the cryoprecipitate thrombin bonding. The enhancement quotient of the retrieved tensile break force values, calculated as the ratio of cryoprecipitate bonding (b) to suturing (c), becomes evident in 7 days (1.32) and persists throughout the 90 days (1.55) corresponding to 32 and 55 percent superiority or marked advantage, respectively, with the cryoprecipitate bonding.

In this Example a low-medium molecular weight grade of CMC-Na was used for the indicated progressive concentration range and successfully extended to numerous other medium and higher molecular grades of CMC-Na at correspondingly lower concentrations limited only to reasonable fluid viscosity. Other commercial grades known as Sodium Carboxymethyl Cellulose Grade P-125-H (Du Pont Company), and Aqualon (TM) Sodium Carboxymethylcellulose, Type 7H (Aqualon Company), are of approximately or reasonably equivalent in vitro qualifications.

EXAMPLE V

The phase transfer process as described in this Example is used to supplement the initial plasma with admixtures of derived plasma fractions such as serum, globulins, and albumin as well as derived biological macromolecular products such as hyaluronic acid, gelatin, natural and derived dextrans, and so on in order to enhance the productivity and augment the composition of cryoprecipitates with other native sources and modified derivatives of mucoprotein and mucopolysaccharide contents.

In this Example human albumin serving as a model for such macromolecular supplementation is used in a range of compositions with plasma as an extension of Example IV for cryoprecipitation into the transfer phase media prepared with CMC-Na. Albumin is chosen to illustrate supplementing the sparing limitations of the amounts of autologous plasma that can be drawn for clinical tissue bonding or for sealant applications especially in pediatric cases, elderly patients, and for special blood types requiring viral-free plasma.

A progressive doubling series starting from 0 (control), 10, 20, and 40 percent albumin (Human, USP, 25 percent solution, Baxter Corp.) as replacement of plasma is processed essentially as described in the preceding Example IV. In each of the four aliquot polypropylene centrifuging tubes, 0.40 gram of CMC-Na, moderate viscosity grade, is dissolved in a transfer phase of 3 ml of warm sterile water, over each of which is placed 38 ml of the plasma-albumin containing 0.02 gram epsilon-amino-n-caproic acid (EACA) and 0.9 ml saline Kefzol (Lilly), cefazoline antibiotic solution (330 mg per mil) in a polypropylene centrifuging tube described in preceding examples; the corresponding transfer processing volumes correspond to a ratio of 19:1. The polypropylene tube contents are capped and processed as follows.

Following cryofreezing at −80° C. for 1 hour, the polypropylene tube contents with the lower phase transfer media are placed directly into the 4-piece Du Pont B-4 Sorvall Superspeed Centrifuge pre-set to +14° C. for simultaneous thawing-centrifuging time of 32 minutes; the controlling temperature in this Example was increased from +10° to +14° C. in order to decrease the residual icing of the solidus state from 30 to 40 percent to about 10 percent with corresponding increase in the solubilizing liquidus state thereby extending the cryoprecipitate series of Fractions to include the supplementing macromolecular entities with repeated re-cycling of the recovered supernatants. The residual icing plug and fluid supernatant are decanted from the sedimented syrupy phase of cryoprecipitate, weighed separately and reconstituted to complete liquidus state and recycled for ensuing series of cryoprecipitate Fractions for the combined accumulative productivity of the valuable cryoprecipitated concentrates for tissue bonding and sealant applications.

TABLE 4c

Summary of In Vivo Rat Incision Tissue Healing
Tensile Break Force - lb-f/in-w
(Thrombin-Calcium Activation)

| Retrieval Days | 4 | 7 | 14 | 28 | 60 | 90 |
|---|---|---|---|---|---|---|
| (a) control tissue* | 76.4 | 82.3 | 78.1 | 80.8 | 90.5 | 77.9 |
| (b) Cryoprecipitate | 0.60 | 2.85 | 5.50 | 24.3 | 62.4 | 75.3 |
| (retrievals) | (5) | (4) | (5) | (6) | (6) | (5) |
| % Tissue regain** | 0.79 | 3.46 | 7.17 | 30.1 | 69.0 | 96.7 |
| (c) Suture, reference | 0.58 | 2.16 | 4.13 | 13.5 | 48.4 | 48.7 |
| (retrievals) | (5) | (5) | (5) | (6) | (6) | (5) |
| % Tissue regain** | 0.76 | 2.62 | 5.29 | 16.7 | 53.5 | 62.5 |
| (d) Enhancement ratio*** | 1.03 | 1.32 | 1.36 | 1.80 | 1.28 | 1.55 |

*Tensile break strength of control tissue adjacent to site of retrieved, healed incision.
**Tensile break strength regained compared to that of the corresponding control.
***Calculated from (b)/(c).

Productivity

As summarized in Table 5a, the productivity in terms of dry solids content in milligrams, column item (d), of each of the plasma-albumin composition series increases consistently and substantially, compared to that of the control with no albumin, indicated as the 100/0 composition, throughout the first three Fraction series but with declining productivity in the last Fraction IV obviously due to the depletions with the preceding Fractions. Significant enhancement ratios over the 100/0 control in the first three Fractions, as to be expected, diminishes with the last Fraction IV. Correspondingly the enhancement ratio, item (e), generally increases with the increasing percentage of the albumin, particularly in Fractions II and III with indications, from decreased productivity in Fraction IV, of practically complete depletion (96.6 percent) of the initial plasma solids in the case of the 40 percent albumin composition with an aggregate cryoprecipitate total of 6365 milligrams.

TABLE 5a

Enhanced Human Plasma Cryoprecipitate Productivity
Supplementation with Human Albumin Phase
Transfer into Sodium Carboxymethylcellulose Medium Cryofreezing: −80° C. 1 hour
Thawing: simultaneous with centrifuging
Centrifugation: +10° C. 32 minutes
Unit process volume: 38 ml plasma + albumin series
Phase transfer volume: 2 ml sterile water
Initial phase solids: (8.7% + 25.0% albumin source)

| Composition | | Rsdl | Yld | Slds | Dry solid | Enhcmnt |
|---|---|---|---|---|---|---|
| plasma % | albumin % | Icing % | grams | Assay % | content mg | (w/alb) ratio |
| FRACTION I | | (a) | (b) | (c) | (d) | (e) |
| 100 | 0 | 13 | 7.57 | 17.9 | 1355 | 1.0 |
| 90 | 10 | 13 | 8.35 | 20.3 | 1695 | control |
| 80 | 20 | 13 | 8.20 | 19.0 | 1558 | 1.25 |
| 60 | 40 | 13 | 9.65 | 23.5 | 2268 | 1.15 |
| | | | | | | 1.67 |

TABLE 5a-continued

Enhanced Human Plasma Cryoprecipitate Productivity
Supplementation with Human Albumin Phase
Transfer into Sodium Carboxymethylcellulose Medium Cryofreezing: −80° C. 1 hour
Thawing: simultaneous with centrifuging
Centrifugation: +10° C. 32 minutes
Unit process volume: 38 ml plasma + albumin series
Phase transfer volume: 2 ml sterile water
Initial phase solids: (8.7% + 25.0% albumin source)

| Composition plasma % | albumin % | Rsdl Icing % | Yld grams | Slds Assay % | Dry solid content mg | Enhcmnt (w/alb) ratio |
|---|---|---|---|---|---|---|
| FRACTION II | | (a) | (b) | (c) | (d) | (e) |
| 100 | 0 | 11 | 1.89 | 22.0 | 416 | 1.0 |
| 90 | 10 | 11 | 3.13 | 23.3 | 729 | control |
| 80 | 20 | 11 | 2.74 | 30.2 | 828 | 1.75 |
| 60 | 40 | 11 | 6.39 | 33.2 | 2121 | 1.99 |
| | | | | | | 5.10 |
| FRACTION III | | (a) | (b) | (c) | (d) | (e) |
| 100 | 0 | 13 | 1.67 | 22.6 | 377 | 1.0 |
| 90 | 10 | 13 | 3.05 | 23.7 | 723 | control |
| 80 | 20 | 13 | 6.40 | 28.7 | 1837 | 1.92 |
| 60 | 40 | 13 | 6.24 | 29.1 | 1816 | 4.87 |
| | | | | | | 4.82 |
| FRACTION IV | | (a) | (b) | (c) | (d) | (e) |
| 100 | 0 | 8 | 2.55 | 25.0 | 638 | 1.0 |
| 90 | 10 | 8 | 2.89 | 20.3 | 587 | control |
| 80 | 20 | 8 | 2.24 | 15.7 | 352 | 0.93 |
| 60 | 40 | 8 | 1.48 | 10.8 | 160 | 0.55 |
| | | | | | | 0.25 |

Note: Parenthetical (proportions) imply continuity from the initial proportions to and through the recycled supernatants, not corrected for aqueous depletions with the concentrates.
Rsdl = Residual, Yld = yield, Slds = Solids, Enhcmnt (w/alb) = Enhancement with albumin

Materials Balance

Table 5b provides a complete materials balance, expressed in milligrams, in accounting for the total productivity based on (A) input from composition products and the corresponding (B) output of accountable cryoprecipitates. The input products include the clottable fibrinogen, item (f), of the cryoprecipitate and the residual associated proteins, item (g), assayed as described the preceding application, Ser. No. 07/855,752, now abandoned. Such complete materials accounting is an essential requirement for assessing productivity of a process engineering system, in this instance of the application, involving re-cycling all or substantially all recoverable supernatant contents for the complete range of the four plasma-albumin compositions as summarized in Table 5b. The product data in Table 5b is derived from the data in Table 5a normalized to consistent standard milligram units for the gram product yield, the fractional percent assay, and the resulting dry solids content as a unit process yield, and the overall connotation productivity.

The total process yields of all combined four Fractions of each plasma-albumin composition increase progressively from the control (100/0) of 75.2 percent to substantially complete, 96.5 percent process yield at the (60/40) composition with indications of attaining cryoprecipitable fractions increasing albumin to about 10/90 plasma/composition range and even with 100 percent albumin. It is noteworthy and a surprising discovery that clottable assay, indicated in Items (f) and (g) in Table 5b as fibrinogen, persists even to predominantly albumin (60/40) composition; the identity or source may be either from remnants of fibrinogen of the plasma or from albumin or from complex interaction of the plasma and albumin. Providing qualification properties are acceptable, supplementation or replacement of a significant proportion of the plasma with albumin provides a material advantage, or even a necessity to use albumin with plasma sources of fibrinogen concentrates where sparing use of autologous plasma are inadequately dictated for in vivo tissue bonding. A separate collateral series of recovered supernatants with the same transfer medium as expected increased the process yield over 90 percent total process yield (Item (1)) in two rather than three supernatant recycles.

TABLE 5b

Productivity - Materials and Products Balance
Supplementation with Human Albumin
Phase Transfer into Carboxymethylcellulose Sodium Medium
(Continued from Table 5a)

| Composition Proportions | | | | |
|---|---|---|---|---|
| Human plasma % | 100 | 90 | 80 | 60 |
| Human albumin % | 0 | 10 | 20 | 40 |
| Composition Volumes | | | | |
| Human plasma ml | 38.0 | 34.2 | 30.4 | 22.8 |
| Human albumin ml | 0 | 3.8 | 7.6 | 15.2 |
| (A) Input from Compositions milligrams | | | | |
| (a) Plasma 8.7% solids | 3306 | 2995 | 2645 | 1984 |
| (b) Albumin 26.8% solids | 0 | 1018 | 2037 | 4047 |
| (c) Total | 3306 | 4013 | 4682 | 6058 |
| (d) CMC-NA mgm | [400] | [400] | [400] | [400] |
| (e) Total, (c) + (d) mgm | 3705 | 4413 | 5082 | 6458 |
| (f) Fibrinogen, cltb. mgm | 1481 | 895 | 524 | 339 |
| (g) Fibrinogen, cltb. % | 44.8 | 22.3 | 11.2 | 5.6 |
| (h) Residual protein mgm | 1825 | 3118 | 4158 | 5719 |
| (i) Residual protein % | 55.2 | 77.1 | 88.8 | 90.4 |
| (j) Fibrinogen protein ratio | 0.812 | 0.287 | 0.126 | 0.593 |
| (B) Output Accountable - Cryoprecipitates | | | | |
| (k) Total Fractions mgm | 2786 | 3734 | 4575 | 6360 |
| (l) Total process yield % | 75.2 | 84.6 | 93.4 | 98.5 |
| (m) Total process loss % | 24.8 | 15.4 | 6.6 | 1.5 |

Qualification Tests—Viscosity and Tensile Break Strength

Table 5c summarizes the qualification properties of syringe viscosity relative to glycerine and tensile break force testing on heretofore described the one-half inch wide edge-joined chamois tissue incision at the mid-section of 3-inch length test sections bonded spectrally by 4 second exposure in a microwave oven as a means of replicating the replicate inherent thermodynamic mechanism of the passive thrombin activation when used in in vivo tissue bonding.

Viscosity

In this progressive series of human plasma replacement with human albumin, the change from the low-medium viscosity grade used in Example IV, to a medium-high viscosity grade of CMC-Na grade in the transfer media imparted a significant increase of about 24 percent in the syringe viscosity of Fraction I in this Example V about 2-fold increase throughout the progressive albumin replacement series. In the ensuing recycled Fraction series the increase in viscosity from recovered supernatants was irregular with compositions of albumin and overall marginal but considerably decreased from the corresponding Fraction I series and this for the reason on that no phase transfer medium was utilized being made part of the separated yields of Fraction I. The entire viscosity range of the concentration series of Fractions proved suitable in syringe application for direct contact adhesion to the surface edges in the ensuing chamois bonding tests.

TABLE 5c

Enhanced Human Plasma Cryoprecipitate Qualifications
Supplementation with Human Albumin
(Continued from Table 5a)
Effect on Viscosity and Tissue Bonding Strength

| Composition | | Viscosity, relative. (glycerol standard)* centipoises | Bonding strength (chamois test)** lb-f/in-w |
|---|---|---|---|
| Plasma % | Albumin % | | |
| FRACTION I | | | |
| 100 | 0 | 103 | 7.6 |
| 90 | 10 | 225 | 10.8 |
| 80 | 20 | 232 | 12.5 |
| 60 | 40 | 217 | 10.6 |
| FRACTION II | | | |
| 100 | 0 | 94 | 9.00 |
| 90 | 10 | 106 | 8.80 |
| 80 | 20 | 94 | 14.1 |
| 60 | 40 | 121 | 12.9 |
| FRACTION III | | | |
| 100 | 0 | — | 3.60 |
| 90 | 10 | 112 | 8.80 |
| 80 | 20 | 105 | 10.75 |
| 60 | 40 | 119 | 7.10 |
| FRACTION IV | | | |
| 100 | 0 | 103 | — |
| 90 | 10 | 95 | — |
| 80 | 20 | 103 | — |
| 60 | 40 | 80 | — |

Tensile Break Strength

Table 5c summarizes the in vitro tensile break force for the entire series of cryoprecipitate Fractions of the progressive plasma-albumin series concentration of the bonding tensile strength using spectral absorption heating by means of microwave at 4 seconds. In general, it is evident that the overall bonding strength has been nearly double to an aggregate average of about 10 lb/in with the medium viscosity grade of CMC-Na compared to an aggregate average of about 5 lb/in using the low-medium viscosity grade of CMC-Na as described in previous Example IV.

In each of the Fractions of the progressively increasing albumin concentrations a surprising and consistent maxima in the bonding tensile break force was made evident at the 20 percent albumin proportion. In the Fraction I series the plasma/albumin ratio could be extended to about 50/50 ratio to approximate the tensile break strength of the plasma (100/0) control of 7.6 foot-pound tensile break strength. By applying a second order polynomial statistical calculation the albumin replacement of the fibrinogen could be increased to any specified tensile break strengths, for instance, for 2 to 3 foot-pound level, more than adequate for in vivo tissue bonding qualification the albumin proportion could be increased to about 60 percent or 40/60 proportion. Similarly in the case of the Fraction II series for the same tensile break level force the albumin could be increased to about 80 percent or 20/80 proportion and in the case of the Fraction III series to about 48 percent of 52/48 proportion. Further replacements of the plasma cryoprecipitates with albumin and with its derived fraction with up to about 95 percent of 05/95 proportions can be useful for tissue bonding or sealants as the dimensional incisions are decreased from the 6 centimeters to millimeter lengths as in microsurgical tissue bonding or sealing.

These examples indicate that the process and products as heretofore discoursed can lead to extensive variations of productivity as shown in Table 5b. This Example provides a salient means for extending resitrictive autologous clinical human plasma for tissue sealant applications supplemented with the more generally available albumin, serum, and other blood fractions including special certified viral-free preparations.

EXAMPLE VI

This Example describes the application of the phase transfer cryoprecipitation process using polyvinyl pyrrolidone (PVP) as another macromolecular chemical type for preparing cryoprecipitates with enhanced productivity and enhanced product qualifications specified in terms of viscosity and tensile break strength for rejoining incised tissue or as tissue sealants.

A progressive doubling series is prepared in a manner similar to that described in the preceding Example IV, B, using 0.05, 0.10, 0.20, and 0.40 gram of high viscosity PVP, PVP-360 grade, average molecular weight of 360,000 daltons, Sigma Chemical Company, dissolved in 3 ml sterile warm water, as the phase transfer layer, in 40-ml polypropylene centrifuging tubes. To each tube is added 0.02 of epsilon-amino-n-caproic acid (EACA) as stabilizer and 0.9 ml saline solution of Kefzol (Lilly), cefazolin sodium antibiotic solution (330 mg per ml) with vortexing to ensure homogenous dissolving. To each tube is next added 35 ml of human plasma, warmed from frozen storage over the bottom phase transfer layer forming a total fluid volume of 38 ml the same volume of plasma used for the non-phase transfer control; the corresponding ratio of initial plasma to phase transfer medium is rated as 19:1.

The capped polypropylene tube contents are placed directly into the 4-place Du Pont swinging buckets provided for the Du Pont Sorvall Superspeed Centrifuge pre-set to controlling +10° C. for the centrifuging time of 32 minutes at 8000 xg. The selected temperature-time schedule with the indicated centrifugal force thereby controls the simultaneous thawing throughout the critical solidus—liquidus equilibrium transition to a residual icing of at least 5 percent. After the completion of the centrifuging and decanting of the supernatants, usually reserved for re-cycling as necessary, the resulting cryoprecipitates are assayed for the detailed materials balance for productivity, namely, yields, percent solids, dry solids content, and for enhancement ratios over the controls.

Table 6a summarizes the productivity in terms of dry solids content in milligrams, item (d), in the progressive range of 1.67 to 13.3 percent concentration of PVP in the transfer phase. The productivity and enhancement ratio commence at 3.34 percent PVP transfer phase concentration after an initial lowering at 1.67 percent PVP phase concentration for reasons related to some critical intermolecular suppression at the phase boundary. The progressive increase above 3.34 percent provides significant and consistent increase in productivity and enhancement ratio over the non-phase control.

Table 6b summarizes the effect of the progressive, increasing concentrations of polyvinylpyrrolidone on the relative viscosity with consistent increases even from the initial low concentration shown in Table 6a although initially inhibitive to productivity. The marked enhancement ratio of the syringe viscosity using polyvinylpyrrolidone with the solids content of about 30 percent makes the cryoprecipitates of this Example adequately qualified for tissue bonding or sealant applications.

The process and derived product features of these Examples can be extended to various modifications in molecular weight grades of PVP, in different phase media other than water, in higher or lower ratios of the plasma to transfer phase volumes, with adjusted electrolyte concentrations of the transfer phase, adjusted thermal drift to higher or lower residual icing, and with re-cycling to maximize the productivity and materials balance as described in preceding Example V.

TABLE 6a

Enhanced Human Plasma Cryoprecipitate Productivity
Phase Transfer into Polyvinylpyrrolidone Media Cryofreezing: −80° C. 1 hour
Thawing: simultaneous with centrifuging
Centrifugation: +10° C. 32 minutes
Unit process volume: 35 ml
Phase transfer volume: 3 ml sterile water
Initial plasma solids: 8.00 percent (2940 mgm/35 ml)

| Polyvinyl pyrrolidone | | Rsd Icn | Yld | Slds Asay | Dry slds content | | Enhancement (corrected)* ratio | |
|---|---|---|---|---|---|---|---|---|
| g | % | % | g | % | mg | | | |
| | | (a) | (b) | (c) | (d) | (e) | (f) | (g) |
| 0 (control)** | | 32 | 1.27 | 34.1 | 433 | — | — | — |
| 0.05 | 1.67 | 8 | 2.03 | 28.4 | 277 | (227) | 0.52 | (0.52) |
| 0.1 | 3.33 | 8 | 2.15 | 31.1 | 669 | (599) | 1.55 | (1.38) |
| 0.2 | 6.67 | 8 | 2.24 | 31.7 | 711 | (511) | 1.64 | (1.18) |
| 0.4 | 13.3 | 8 | 3.60 | 30.5 | 1098 | (698) | 2.54 | (1.61) |

*Parenthetic ratios correcting for the progressive series of polyvinyl alcohol, in milligrams, added initially to the transfer phase media.
**Without phase transfer media.
Rsd Icn = Residual Icing, Yld = yield, Slds Asay = Solids Assay TABLE 6b Enhanced Human Plasma Cryoprecipitate Productivity
(Continued from Table 6a)
Effect of Polyvinylpyrrolidone for Enhanced Viscosity

| PVP (phase transfer) | | Viscosity, relative (glycerol standard) | Comparative |
|---|---|---|---|
| Grams | Percent | centipoises, av. | enhancement ratio |
| 0 (control) | | 82 | — |
| 0.05 | 1.70 | 123 | 1.50 |
| 0.1 | 3.40 | 133 | 1.62 |
| 0.2 | 6.30 | 136 | 1.66 |
| 0.4 | 1.60 | 142 | 1.73 |

PVP = Polyvinylpyrrolidone.

The foregoing descriptive and preferred embodiments of the processing system as a continuation-in-part of the application Ser. No. 07/855,752, filed Mar. 23, 1992, now abandoned, are intended to include the therein dimensional range of the surface to volume ratio (S/V) dimensionally in reciprocal centimeters ($cm^2/cm^3$ or 1/cm) of about 1.65/1 as used in the examples of this application to as high as 4.38/1 or higher least depending on the selected dimensional configuration or shape such as a round test tube or a standard plastic blood bag flattened and or constrained in a cryofreezing and centrifuging device or system. The initial plasma, as already described in this application, may be admixed with other human plasma or serum or fractions thereof components. Likewise the transfer media described in the examples can be substituted with the centrifuged supernatant fluid into which is added any of the natural and synthetic macromolecular components for enhanced process productivity or for enhancement of specific product qualification including or in addition to viscosity for contact adhesion or for efficient in vitro or in vivo tissue bonding, passive or spectral. These modifications and equivalents can be either expected or required for optimizing the productivity or a specific in vitro qualification including or supplementing presented in the examples herein. The description and example of rat dorsal skin tissue includes bonding with other variants of physiological tissues such as that of arteries, nerves, membranes, and so on wherein the cryoprecipitates of this invention can be used as fibrin sealants.

Various modifications of the invention in addition to those shown and described herein will be apparent to those skilled in the art from the foregoing description. Such modifications are also intended to fall within the scope of the appended claims.

What is claimed is:

1. A process for producing a concentrate from mammalian plasma comprising:
   (a) cryofreezing a two phase system comprising an initial plasma phase, having a solidus—liquidus transition temperature, superimposed over an aqueous transfer phase, said aqueous transfer phase containing a soluble polymer;
   (b) thawing to the solidus—liquidus transition temperature for a time sufficient to attain from about 5 weight percent to about 95 weight percent residual icing;
   (c) centrifuging at a controlled temperature, time and gravitational force to within said range of residual icing resulting in a sedimented concentrate and a supernatant; and
   (d) separating the sedimented concentrate by decanting the supernatant and residual icing.

2. The process of claim 1 wherein the thawing operation is carried out simultaneously with centrifuging.

3. The process of claim 1 wherein the volume of the initial plasma phase and the volume of the aqueous transfer phase has a ratio of from about 1:1 to about 40:1.

4. The process of claim 1 wherein the soluble polymer is a polysaccharide of a biological origin.

5. The process of claim 4 wherein the soluble polymer is in a concentration from about 0.05 weight/volume percent to about 50 weight/volume percent.

6. The process of claim 1 wherein the soluble polymer is a polysaccharide selected from the group consisting of pectin, potassium polygalacturonate, hyaluronic acid, chondroitin sulfate, and sodium carboxymethyl cellulose.

7. The process of claim 1 wherein the decanted supernatant fluid is recycled at least once through the sequence of cryofreezing, thawing, centrifuging and decanting operations.

8. The process of claim 1 using human plasma.

9. The process of claim 1 using a mixture of human plasma and albumin.

10. The process of claim 1 using bovine plasma.

11. The process of claim 6 wherein said soluble polymer is a carboxylate salt of cellulose.

12. A process of claim 1 wherein the soluble polymer is polyvinylpyrrolidone.

* * * * *